United States Patent [19]

Anderson et al.

[11] Patent Number: 5,795,886
[45] Date of Patent: Aug. 18, 1998

[54] DIHYDRO-2,3-BENZODIAZEPINE DERIVATIVES

[75] Inventors: Benjamin A. Anderson, Zionsville; Marvin M. Hansen; Nancy K. Harn, both of Indianapolis, all of Ind.

[73] Assignee: Eli Lilly and Company, Indianapolis, Ind.

[21] Appl. No.: 776,892

[22] PCT Filed: Aug. 30, 1995

[86] PCT No.: PCT/US95/10945

§ 371 Date: Feb. 11, 1997

§ 102(e) Date: Feb. 11, 1997

[87] PCT Pub. No.: WO96/06606

PCT Pub. Date: Mar. 7, 1996

Related U.S. Application Data

[63] Continuation-in-part of Ser. No. 413,029, Mar. 28, 1995, abandoned, which is a continuation-in-part of Ser. No. 298,645, Aug. 31, 1994, abandoned.

[51] Int. Cl.$^6$ .......................... A61K 31/55; C07D 243/02
[52] U.S. Cl. .............................. 514/220; 540/557
[58] Field of Search .......................... 540/557; 514/220

[56] References Cited

U.S. PATENT DOCUMENTS 5,459,137  10/1995  Andrasi et al. .................. 514/220

OTHER PUBLICATIONS

Bioorganic & Medical Chemistry Letters, Tarnawa et al., vol. 3, No. 1, pp. 99–104, 1993.

*Primary Examiner*—Yogendra N. Gupta
*Attorney, Agent, or Firm*—Martin A. Hay; David E. Boone

[57] ABSTRACT

Compounds having general formula (I) wherein R is hydrogen or $C_1$–$C_{10}$ alkyl; X is an aromatic moiety selected from phenyl, thienyl, furyl, pyridyl, imidazolyl, benzimidazolyl, benzothiazolyl and phthalazinyl which is unsubstituted or substituted with one or more moieties chosen from the group consisting of halogen, hydroxy, cyano, nitro, $C_1$–$C_6$ alkyl, $C_3$–$C_6$ cycloalkyl, $C_1$–$C_4$ alkoxy, carboxy, $C_1$–$C_6$ alkoxycarbonyl, acetyl, formyl, carboxymethyl, hydroxymethyl, amino, aminomethyl, methylenedioxy and trifluoromethyl; and "Aryl" represents p-nitrophenyl, p-aminophenyl or p-(protected amino) phenyl; or a pharmaceutically acceptable salt thereof, are useful as anticonvulsants.

13 Claims, No Drawings

DIHYDRO-2,3-BENZODIAZEPINE DERIVATIVES

This application is a continuation-in-part of application Ser. No. 08/413,029 filed Mar. 28, 1995, (now abandoned), which is a continuation-in-part of application Ser. No. 08/298,645 filed Aug. 31, 1994 (abandoned).

FIELD OF THE INVENTION

This invention relates to novel dihydro-2,3-benzodiazepine derivatives, to a process for their preparation, to pharmaceutical compositions containing them and to their use as AMPA receptor antagonists.

BACKGROUND OF THE INVENTION

U.S. Pat. No. 4,835,152, European patent application publication number EP-A1-0492485 and International patent application publication number WO 92/11262 disclose certain dihydro-2,3-benzodiazepine derivatives possessing central nervous system effects, in particular muscle-relaxant and anticonvulsant activity, as well as antidepressive and antiparkinsonian activity. The structure activity relationships of these compounds are discussed in Tarnawa et al; Bioorganic and Medicinal Chemistry; Letters, Vol. 3, No. 1, pp 99–104, 1993.

Compounds having an acetyl, propionyl or N-methylcarbamoyl group at the 3-position of the benzodiazepine ring are reported to be the most potent, and those with a benzoyl or phenylacetyl group amongst the least potent.

Surprisingly, it has been found that certain dihydro-2,3-benzodiazepines having an aromatic group attached directly to the 3-position of the benzodiazepine ring and a p-aminophenyl group attached to the 1-position possess potent anticonvulsant activity.

SUMMARY OF THE INVENTION

The present invention provides a compound having the general formula:

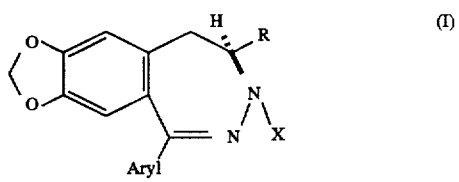

wherein R is hydrogen or $C_1$–$C_{10}$ alkyl;

X is an aromatic moiety selected from phenyl, thienyl, furyl, pyridyl, imidazolyl, benzimidazoyl, benzothiazolyl and phthalazinyl which is unsubstituted or substituted with one or more moieites chosen from the group consisting of halogen, hydroxy, cyano, nitro, $C_1$–$C_6$ alkyl, $C_3$–$C_6$ cycloalkyl, $C_1$–$C_4$ alkoxy, carboxy, $C_1$–$C_6$ alkoxycarbonyl, acetyl, formyl, carboxymethyl, hydroxymethyl, amino, aminomethyl, methylenedioxy and trifluoromethyl; and "Aryl" represents p-nitrophenyl, p-aminophenyl or p-(protected amino)phenyl;

or a pharmaceutically acceptable salt thereof.

DETAILED DESCRIPTION OF THE INVENTION

The compounds of formula I in which "Aryl" represents p-nitrophenyl or p-(protected amino)phenyl are useful as intermediates in the preparation of compounds of formula I in which "Aryl" represents p-aminophenyl. Certain compounds of formula I in which "Aryl" represents p-(protected amino)phenyl may also be useful as pro-drugs for compounds of formula I in which "Aryl" represents p-aminophenyl.

As used herein, the term "$C_1$–$C_{10}$ alkyl" represents a straight or branched alkyl chain having from one to ten carbon atoms. Typical straight or branched $C_1$–$C_{10}$ alkyl groups include methyl, ethyl, n-propyl, isopropyl, n-butyl, isobutyl, sec-butyl, t-butyl, n-pentyl, isopentyl, n-hexyl, 2-methylpentyl, n-octyl, decyl and the like. The term "$C_1$–$C_{10}$ alkyl" includes within it the terms "$C_1$–$C_4$ alkyl" and "$C_1$–$C_6$ alkyl".

Examples of values for an aromatic moiety represented by x are phenyl, 2-thienyl, 3-thienyl, 2-furyl, 2-pyridyl, 2-imidazolyl, 2-benzimidazolyl, 2-benzothiazolyl and 1-phthalazinyl.

Particular values for substituents which may be present on an aromatic moiety represented by X are fluoro, chloro, bromo, iodo, hydroxy, cyano, nitro, methyl, methoxy, carboxy, methoxycarbonyl, acetyl, formyl, carboxymethyl, hydroxymethyl, amino, aminomethyl and trifluoromethyl.

Examples of values for X are phenyl, 4-methyphenyl, 2-methylphenyl, 4-methoxyphenyl, 4-(i-propyl)phenyl, 4-(t-butyl)phenyl, 4-acetylphenyl, 4-trifluoromethylphenyl, 4-chlorophenyl, 2-bromophenyl, 3-iodophenyl, 3,4-methylenedioxyphenyl, 2-methoxycarbonylthien-3-yl, 2-pyridyl, 2-benzimidazolyl, 2-benzothiazolyl and 1-phthalazinyl.

"Aryl" used in the formulae throughout the specification represents p-nitrophenyl, p-aminophenyl and p-(protected amino)phenyl such as p-($C_1$–$C_6$ alkanoylamino)phenyl, for example p-acetylaminophenyl. Examples of suitable protecting groups may be found in McOmie, Protective Groups in Organic Chemistry, Plenum Press, N.Y., 1973, and Greene and Wuts, Protecting Groups in Organic Synthesis, 2nd ed., John Wiley and Sons, N.Y., 1991. Preferably "Aryl" represents p-aminophenyl.

R preferably represents a $C_1$–$C_3$ alkyl group, for example methyl.

X preferably represents phenyl, 2-pyridyl, 2-methoxycarbonylthien-3-yl, 2-benzimidazolyl, 2-benzothiazolyl or 1-phthalazinyl. The 2-pyridyl group is especially preferred.

The compounds of general formula I may be prepared by cyclising a compound having the general formula

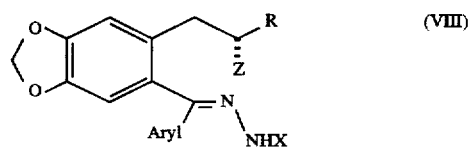

wherein Z represents a leaving atom or group, to afford a compound having the general formula I, whereafter, if desired, converting the compound of formula I into another compound of formula I and/or forming a pharmaceutically acceptable salt.

The leaving atom or group represented by z may be for example, a halogen atom or an organosulfonyloxy group, or may be generated in situ from the corresponding compound of formula VIII in which Z represents hydroxy.

Particular values for Z when it represents a halogen atom are chlorine and bromine.

An organosulfonyloxy group represented by Z may be, for example, or $C_1$–$C_4$ alkanesulfonyloxy group, a trifluoromethanesulfonyloxy group or a phenylsulfonyloxy group in which the phenyl group is unsubstituted or substituted by one or two substituents selected independently from $C_1$-$C_4$ alkyl, $C_1$-$C_4$ alkoxy, halogen, nitro and halo $C_1$-$C_4$ alkyl. Particular values for Z are methanesulfonyloxy, phenylsulfonyloxy, p-toluenesulfonyloxy and p-nitrophenylsulfonyloxy.

Preferably Z is an organosulfonyloxy group.

When Z represents a halogen atom or an organosulfonyloxy group, the cyclisation is preferably performed in the presence of a base selected from alkali metal hydroxides, for example sodium or potassium hydroxide; alkali metal carbonates, for example sodium or potassium carbonates; alkali metal hydrides, for example sodium or potassium hydride; and alkali metal alkoxides, for example lithium, sodium or potassium t-butoxide. The process is conveniently performed at a temperature in the range of from –30° to 100° C., preferably from 0° to 50° C. Suitable solvents include alkanols such as methanol or ethanol, and ethers such as tetrahydrofuran.

A compound of formula VIII in which Z represents a leaving atom or group may be generated in situ by reacting a compound of formula VIII in which Z represents a hydroxyl group with a triarylphosphine in the presence of an azidodicarboxylate ester. The reaction is analogous to the well known Mitsunobu reaction. Preferably the triarylphosphine is triphenylphosphine and the azodicarboxylate ester is diethyl azodicarboxylate. The process is conveniently performed at a temperature in the range of from –30° to 100° C., preferably from –10° to 50° C. Suitable solvents include ethers such as tetrahydrofuran. It will be appreciated that in this instance, the leaving group represented by Z is a triarylphosphonyloxy group such as triphenylphosphonyloxy.

The compounds of formula (I) in which Aryl represents p-aminophenyl may be prepared by cyclising a compound of formula VIII in which Aryl represents p-nitrophenyl, p-aminophenyl or p-(protected amino)phenyl, whereafter, if necessary, (a) reducing a p-nitrophenyl group to afford a p-aminophenyl group, or (b) deprotecting a p-(protected amino)phenyl group to afford a p-aminophenyl group.

The nitro group in a p-nitrophenyl group may be reduced by a method known in the art, for example as described in EP-A1-492485. Thus it may be reduced by reaction with hydrazine or hydrazine hydrate in the presence of a Raney nickel catalyst. Alternatively, it may be reduced by reaction with hydrogen, formic acid, ammonium formate, a trialkylammonium formate such as triethylammonium formate, or an alkali metal formate such as sodium formate or potassium formate, in the presence of a Group VIII metal catalyst, such as palladium on charcoal. Suitable solvents include alcohols such as methanol, ethanol or isopropanol, and ethers such as tetrahydrofuran or acetone. The reduction may conveniently be performed at a temperature in the range of from –10° to 120° C.

The protecting group in a p-(protected amino)phenyl group may be removed in a conventional way. For example, a $C_{1-6}$ alkanoyl group may be removed by hydrolysis in the presence of a mineral acid, for example hydrochloric acid.

The compounds of general formula VIII may be prepared by a multistep process, starting from a methylenedioxyphenyl ketone derivative. This process comprises the steps below.

a) providing a quantity of a compound having the formula:

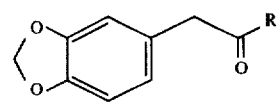

b) asymmetrically reducing the compound of formula II to yield a compound having the formula:

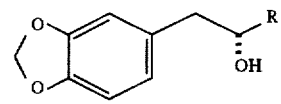

c) reacting the compound of formula III with an arylaldehyde compound of formula Aryl.CHO to yield an isochroman compound having the formula:

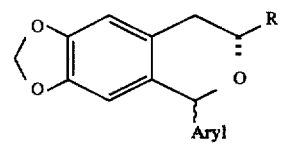

d) reacting the compound of formula IV with an oxidizing agent to yield a compound of the formula:

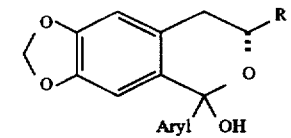

e) reacting the compound of formula V with a hydrazine derivative of formula $H_2NNHX$ to yield a compound of the formula:

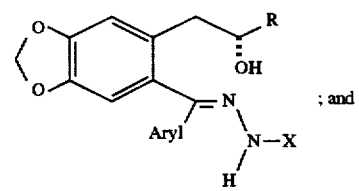

; and f) reacting the compound of formula VI with a (i) sulfonyl halide reagent and a base, to form an intermediate sulfonate, followed by reacting the resultant sulfonate with a strong base; or (ii) by direct Mitsunobu cyclization in which the compound of formula VIII is generated in situ, then cyclises directly to yield the compound of formula I.

The preferred process involves the early chiral reduction of a ketone to an alcohol. Substituents are added in a multi-step process to close the benzo-fused pyran ring, before a hydrazine reagent is introduced to open the ring and add the necessary nitrogen components. Finally, the secondary ring is closed by addition of a strong base and the compound is reduced to form the desired compound.

Most preferably, the chiral reduction step is the initial step in the synthesis of the Formula (I) compounds from ketones. The chiral reduction may be effected by use of specific chemicals or, preferably, by using biological agents as disclosed below. Setting the stereochemistry early in the process is beneficial and allows for the later steps to be carried out on relatively enantiomerically pure material. This increases both throughput and enantiomeric purity.

The first step of the process involves a chiral reduction of the starting material (preferably a 3,4-methylenedioxyphenyl acetone derivative) to produce a virtually enantiomerically pure alcohol derivative of 1,2-methylenedioxybenzene. Preferably, the enantiomer formed is the (S) or (+) stereoisomer of the alcohol. The most preferred starting compound is 3,4-methylenedioxyphenyl acetone.

Alternatively, the initial step may involve the combination of a halo derivative of 1,2-methylenedioxybenzene with an enantiomerically enriched epoxide. This also results in the production of a highly enantiomerically enriched alcohol derivative of 1,2-methylenedioxybenzene.

The material used to effect the chiral reduction initial step may be either chemical or preferably biological. In the case of biological agents, the preferred agents are reducing enzymes, most preferred being yeasts from the Zygosaccharomyces group. Other biological agents which may be used include: *Pichia fermentans, Endomycopsis fibuligera, Nematospora coryli, Saccharomyces sp., Candida famata, Saccharomyces pastorianus, Saccharomyces cerevisiae, Saccharomyces uvarum, Candida utilis, Saccharomyces globosus, Kluyveromyces dobzhansk, Kluyveromyces lactis, Candida albicans,* bakers' yeast, *Zygosaccharomyces rouxii, Lactobacillus acidophilus, Aureobasidium pullulans, Mortierella isabellina, Rhizopus oryzae, Kloeckeva javanica, Hanseniaspora valbyensis, Octosporomyces octospori, Candida guilliermondi, Candida parapsilosis, Candida tropicalis, Torulopsis taboadae, Torulopsis ethanolitolerans, Torulopsis ptarmiganii, Torulopsis sonorensis, Trigonopsis variabilis, Torulopsis enokii, Torulopsis methanothermo,* SAF instant yeast, ashland yeast inact., *Candida boidinii, Candida blankii* and Red Star yeast.

The desired intermediate formed in the initial step is an alcohol substituted congener of 1,2-methylenedioxybenzene, with the most preferred congener consisting of (S)-α-Methyl-1,3-benzodioxole-5-ethanol.

The desired intermediate compound formed in the initial step is then subjected to a Pictet-Spengler reaction which provides for convergent fusion of the benzodiazepine carbon constituents. The preferred reagent of choice is p-nitrobenzaldehyde, although other reagents known to those skilled in the art such as acetals may be used. The preferred intermediates are dihydrobenzopyrans with the most preferred compound being 7,8-dihydro-7-methyl-5-(4-nitrophenyl)-5H-1,3-dioxolo-benzo[b]pyran.

The dihydrobenzopyran congener is then oxidized at the C5 position to yield a hemiketal derivative of the general formula

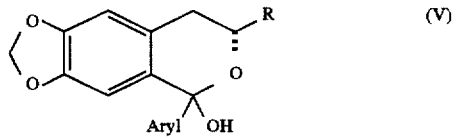

The preferred oxidizing agents include potassium permanganate, DDQ (2,3-dichloro-5,6-cyano-1,4-benzoquinone) or others, with the most preferred agent being a sodium hydroxide and air combination.

The C5-hemiketal is then reacted with a hydrazide derivative of formula $H_2NNHX$ in the presence of acid in order to form the hydrazone intermediate of formula VI. The reaction is conveniently performed under reflux in an aromatic or protic solvent. In this step, the benzopyran ring is opened such that the hydrazone component becomes attached to the $C_5$ carbon.

The hydrazone derivative is converted into the desired benzodiazepine ring via intramolecular alkylation. This is accomplished by one of several possible methods. The first method involves the addition of a mixture of a sulfonyl halide reagent of formula $YSO_2X^a$ in which $x^a$ represents a halogen atom such as chlorine and Y represents an organic group such as $C_1$–$C_4$ alkanesulfonyl, trifluoromethylsulfonyl, or phenylsulfonyl in which the phenyl group is unsubstituted or substituted by one or two substituents selected independently from $C_1$–$C_4$ alkyl, $C_1$–$C_4$ alkoxy, halogen, nitro and halo $C_1$–$C_4$ alkyl (for example, methanesulfonyl chloride) and a base, such as a tertiary amine (for example, triethylamine) to form a sulfonate intermediate of formula

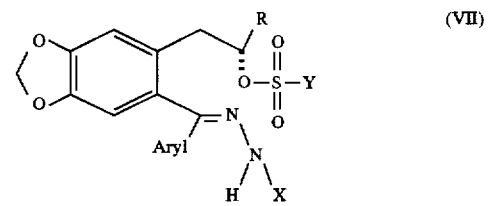

The sulfonate is then converted to the 8,9-dihydro-7H-2,3-benzodiazepine congener by addition of a strong base, most preferably an alkali metal hydroxide such as caustic soda, an alkali metal alkoxide such as sodium or potassium tert-butoxide, an alkali metal carbonate such as potassium carbonate or an alkali metal hydride such as sodium hydride. Optionally the reaction may be performed in the presence of a phase transfer catalyst, such as tetrabutylammonium bromide.

Alternatively, the compound of formula VI may be converted into a compound of formula VIII in which Z represents a halogen atom, for example, a compound of formula VI may be reacted with imidazole, triphenylphosphine and bromine to afford a compound of formula VIII in which Z represents a bromine atom. The resultant compound for formula VIII may then be cyclised following the same procedure as that used for a compound of formula VIII in which Z represents an organosulfonyloxy group.

The use of a compound of formula VIII in which Z represents an organosulfonyloxy group (corresponding with a compound of formula VII) is preferred.

Another method involves a Mitsunobu cyclization which is a one-step process to yield the p-nitrophenyl benzodiazepine intermediate.

When a compound of formula I in which Aryl represents p-aminophenyl is desired, and a compound of formula IV in which Aryl represents p-nitrophenyl has been prepared, the nitro group may be reduced at any stage in the process. Preferably it is reduced after process step e) or f).

The nitro group may be reduced by addition of hydrogen gas or a hydrogen source in the presence of a catalyst. The preferred hydrogen source is potassium formate, or other formate salt (such as ammonium formate), with the preferred catalyst being a combination of palladium metal and activated charcoal. The reduction step is well known to those skilled in the art.

The preferred processes can be summarized by the following schemes to yield the most preferred product.

Scheme (I)

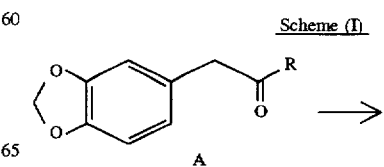

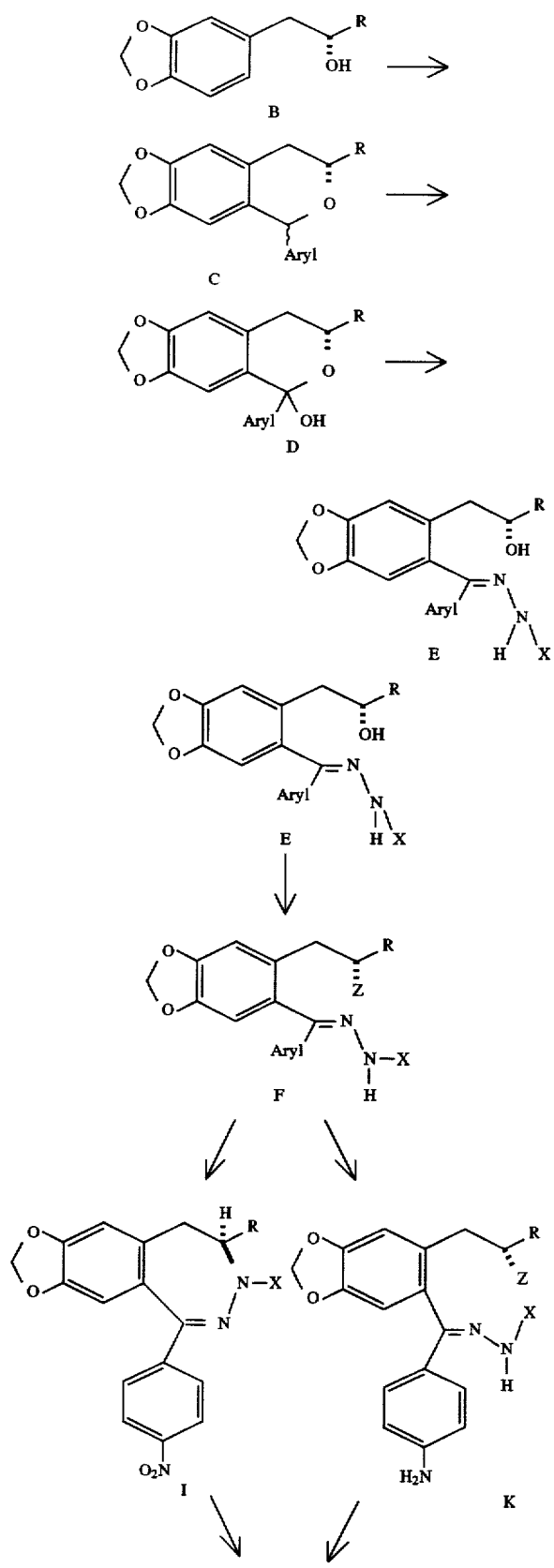

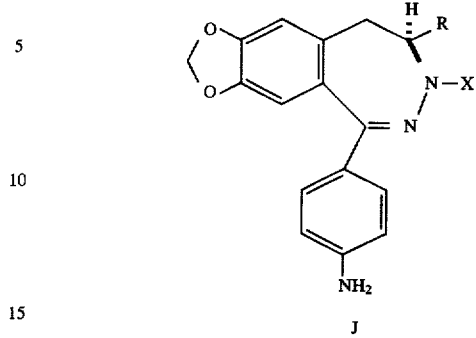

In scheme (I), the initial step of the process involves the addition of biological agents, most preferably *Zygosaccharomyces rouxii*, to reduce the ketone to the desired alcohol. A suitable quantity of an adsorbent resin such as AD-7, XAD-7, HP2MGL (cross-linked polymethacrylates from Rohm & Haas), HP20 (polystyrenic), or SP207 (brominated polystyrene from Mitsubishi) may be added to the reaction mixture to prevent death of the organism and to adsorb the alcohol as it is formed. Other similar resins may also be used.

SCHEME II

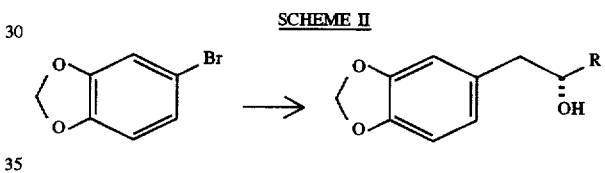

In scheme (II), the initial step of the process involves reacting an aryl halide derivative, such as 4-bromo-1,2-(methylenedioxy)benzene, with an alkali metal hydrocarbon (sec-butyllithium is preferred) and an enantiomerically pure epoxide. Preferred is (S) - (-)-propylene oxide. Alternatively, an aryl halide may first be converted into a Grignard reagent by reaction with magnesium, then reacted with an enantiomerically pure epoxide in the presence of Copper (I) iodide or catalyst. In both scheme (I) and scheme (II), the objective is to set the stereochemistry of the C8 atom of the benzodiazepine ring as early as possible. Both schemes have been observed to accomplish this objective and have formed enantiomerically enriched (ee) alcohols in the 98% purity range.

Compounds of formula I have been found to possess anticonvulsant activity in the test described by J. David Leander, Epilepsia, 33(3), 573–576, 1992. For example, the compound of Example 23 was found to give an $ED_{50}$ of 3.2 mg/kg. The compound of Example 17 has been found to show particularly high potency in this test.

According to another aspect therefore, the present invention provides a method of treating convulsions in a mammal, which comprises administering an effective amount of a compound of formula I, or a pharmaceutically acceptable salt thereof.

It is believed that the formula I compounds of the present invention are antagonists of the AMPA subtype of excitatory amino acid receptors. Therefore, another aspect of the present invention is a method of blocking the AMPA excitatory amino acid receptors in mammals which comprises administering to a mammal requiring decreased excitatory amino acid neurotransmission a pharmaceutically-effective amount of a compound of formula I or a pharmaceutically acceptable salt thereof.

The term "pharmaceutically-effective amount" is used herein to represent an amount of the compound of the invention which is capable of blocking the AMPA excitatory amino acid receptor. The particular dose of compound administered according to this invention will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular, or intranasal routes. Alternatively, the compounds may be administered by continuous infusion. A typical daily dose will contain from about 0.01 mg/kg to about 30 mg/kg of the active compound of this invention. Preferred daily doses will be about 0.05 mg/kg to about 24 mg/kg, more preferably about 0.1 to about 20 mg/kg.

A variety of physiological functions have been shown to be subject to influence by excessive or inappropriate stimulation of excitatory amino acid neurotransmission. The formula I compounds of the present invention are believed to have the ability to treat a variety of neurological disorders in mammals associated with this condition which include acute neurological disorders such as cerebral deficits subsequent to cardiac bypass surgery and grafting, stroke, cerebral ischemia, spinal cord trauma, head trauma, perinatal hypoxia, cardiac arrest and hypoglycemic neuronal damage. The formula I compounds are believed to have the ability to treat a variety of chronic neurological disorders such as Alzheimer's Disease, Huntington's Chorea, amyotrophic lateral sclerosis, AIDS-induced dementia, ocular damage and retinopathy, and idiopathic and drug-induced Parkinson's Disease. The present invention also provides methods for treating these disorders which comprise administering to a patient in need thereof an effective amount of a compound of formula I.

The formula I compounds of the present invention are also believed to have the ability to treat a variety of other neurological disorders in mammals that are associated with glutamate dysfunction including muscular spasms, convulsions, migraine headaches, urinary incontinence, psychosis, drug tolerance and withdrawal, anxiety, emesis, brain edema, chronic pain, and tardive dyskinesia. The formula I compounds are also useful as analgesic agents. Therefore, the present invention also provides methods for treating these disorders which comprise administering to a patient in need thereof an effective amount of a compound of formula I.

The compounds of the present invention are preferably formulated prior to administration. Therefore, another aspect of the present invention is a pharmaceutical composition comprising a compound of formula I and a pharmaceutically-acceptable diluent or carrier. The present pharmaceutical formulations are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate and mineral oil. The formulations can additionally include lubricating agents, wetting agents, emulsifying and suspending agents, preserving agents, sweetening agents, or flavoring agents. Compositions of the inventions may be formulated so as to provide quick, sustained, or delayed release of the active ingredient after administration to the patient by employing procedures well known in the art.

The compositions are preferably formulated in a unit dosage form, each dosage containing from about 5 to about 5000 mg, more preferably about 25 to about 3000 mg of the active ingredient. The most preferred unit dosage form contains about 100 to about 2000 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier. The following formulation examples are illustrative only and are not intended to limit the scope of the invention in any way.

Formulation 1

Hard gelatin capsules are prepared using the following ingredients:

| | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight % |
|---|---|
| Active Ingredient | 0.25 |
| Ethanol | 29.75 |
| Propellant 22 | 70.00 |
| (chlorodifluoromethane) | |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| Active Ingredient | 60 mg |
|---|---|
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg medicament are made as follows:

| Active Ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 sieve, and filled into hard gelatin capsules in 200 mg quantities.

Formulation 6

Suppositories each containing 225 mg of active ingredient may be made as follows:

| Active Ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| Active Ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| Active Ingredient | 100 mg |
|---|---|
| Mannitol | 100 mg |
| 5 N Sodium hydroxide | 200 ml |
| Purified water to total | 5 ml |

The following examples illustrate the invention.

EXAMPLE 1

Synthesis of (S)-α-methyl-1,3 benzodioxole-5-ethanol 1 equiv. of 3,4-methylenedioxyphenyl acetone, 0.45 equiv. disodium phosphate, 0.03 equiv. phosphoric acid, 12.5 volumes AD-7 resin and 5.8 volumes of water were mixed together and stirred for 15–60 minutes at 20°–25° C. 2.27 equiv. of glucose were added and Z. rouxii ATCC 14462 is added in an amount of 1.5 grams wet cell paste per gram of ketone (this is 0.375 grams/gram on a dry basis). This mixture was diluted with water to 25 volumes and then gently stirred at 33°–35° C. for 8–16 hours. The mixture was filtered on a 100 mesh (~150 micron) stainless steel screen, and the resin which was retained by the screen was washed with 25 volumes of water split into 4 separate portions. The product, which was adsorbed to the resin, was then desorbed from the resin with 25 volumes of acetone. The acetone/product solution was then stripped to dryness under vacuum to yield the title intermediate as a yellow, medium viscosity oil. The in-situ yield was 97–100%, while the isolated yield was 85–90%. The potency was 80–95% and the EE is 100%.

EXAMPLE 2

Synthesis of (5RS,7S)-7,8 dihydro-7-methyl-5-(4-nitrophenyl)-5H-1,3 dioxolo-[4,5-G][4,5-G][2] benzopyran The above intermediate was dissolved in 4.64 volumes of toluene, filtered over hyflo, and washed with 1.55 volumes of toluene. 1.05 equiv. p-nitro-benzaldehyde and 1.05 equiv. of conc. hydrochloric acid were added, and the mixture was heated to 55°–65° C. and stirred 1 hour. A solvent exchange was then conducted at 250 mmHg, replacing the toluene with 12.4 volumes of 93% isopropanol/7% water/ The volume during this solvent exchange varies from 11–14 volumes, and the final volume was ~11 volumes. The mixture was cooled to 0°–10° C. and stirred 1 hour. The needle-like product crystals were filtered and washed 2 times with 1.85 vol. isopropanol and dried under vacuum at 50°–60° C. The in-situ yield of the title compound was 95+% while the isolated yield was 87–93%. The potency was 99+% and the EE is 100%.

EXAMPLE 3

Alternative syntheses of (S)-α-methyl-1,3 benzodioxole-5-ethanol 3.47 grams of 4-bromo-1,2(methylenedioxy)benzene were dissolved in 100 ml of tetrahydrofuran at −78° C., 13.9 ml of 1.3M sec-butyllithium in cyclohexane was then added to consume the aryl halide in less than 30 minutes. 1.00 grams of (S)-(-)-propylene oxide in 2 ml THF was added by syringe and the solution stirred for 45 minutes. The solution was then warmed to 23° C. for 16 hours. The reaction mixture was poured into 3M ammonium chloride solution and the product isolated by extraction with ethyl acetate. The combined extracts were dried over magnesium sulfate filtered through florisil and concentrated by rotary evaporation. The residual oil was purified by silica gel chromatography and eluted with a 50:50 mixture of hexane and diethyl ether to yield 1.40 g (45%) of the subtitled intermediate. Pchem: $[\alpha]_{365}$ +117.2° (c 1.0, $CHCl_3$) TLC $R_f$=0.26 (50:50 hexane:ether); IR ($CHCl_3$) 3598, 3012, 2973, 2887, 1490, 1249, 1041 $cm^{-1}$; $^{13}C$ NMR ($CDCl_3$) d 147.75, 146.19, 132.26, 122.27, 109.68, 108.30; mass spectrum, m/z (FD, $M^+$) 180; Anal. Calcd. for $C_{10}H_{12}O_3$: C, 66.65; H, 6.71. Found: C, 66.42; H, 6.66.

EXAMPLE 4

Alternative Synthesis of (5RS,7S)-7,8-dihydro-7-methyl-5-( 4-nitrophenyl)-5H-1,3-dioxolo-[4,5-G][2]benzopyran 244 grams of p-nitrobenzaldehyde was added to a solution of 300 grams of the intermediate formed in the biocatalyzed reduction step of Example 1 in 4.45 L of toluene. 166.5 mL of concentrated hydrochloric acid was added dropwise over 15–20 min and the resulting mixture was heated to 60° C. for 2.5 h. The mixture was cooled to room temperature and concentrated by rotary evaporation. 3 L of ethanol was added and the mixture was concentrated to a solid. A second 3 L portion of ethanol was added and the mixture was stirred for 1 h. The slurry was cooled overnight and the crystalline product was isolated by vacuum filtration. The filter cake was washed with ethanol and then dried in a vacuum oven at 40°–60° C. to yield 450 g (86%) of an off-white solid which was determined to be an isomeric mixture of the above subtitled optically active intermediate. P Chem: $[\alpha]_{365}$ +55° (c0.4, $CHCl_3$).

EXAMPLE 5

Synthesis of (5RS,7S)-7,8-dihydro-7-methyl-5-(4-nitrophenyl)-5H-1,3-dioxolo[4,5-G][2]benzopyran-5-ol 350 grams of the isomeric intermediate from Example 4 was added to a solution of 731 mL of dimethylsulfoxide and 2923 mL of dimethylformamide. The mixture was cooled to 8°–12° C. and compressed air was passed through the mixture. 117.5 mL of 50% aqueous sodium hydroxide was added in one portion and the resulting mixture was stirred for 4.5 h. The reaction mixture was added by cannula over 30–60 min to 8.25 L of a stirred 1N hydrochloric acid solution at 10°–15° C. The resulting precipitate was filtered and washed with 3 L of water then air dried to a constant weight (384 g). The wet cake was carried into Example 6 without further drying. P chem: Data recorded from a 3:1 isomeric mixture. TLC $R_f$=0.19 (75:25 hexane:ethyl acetate); IR ($CHCl_3$) 3605, 3590, 3015, 3000, 2960, 2910, 1608, 1522, 1484, 1352, 1240, 1042 $cm^{-1}$; $^1H$ NMR ($CDCl_3$, 300 MHz) δ (major isomer) 8.16 (d, 2H, J=6.9 Hz), 7.73 (d, 2H, J=6.9 Hz), 6.55 (s, 1H), 6.38 (s, 1H), 5.86 (s, 1H), 5.83 (s, 1H), 4.38 (M, 1H), 2.70 (m, 2H), 1.39 (d, 3H, J=6.3 Hz); 8 (minor isomer) 8.27 (d, 2H, J=8.9 Hz), 7.90 (d, 2H, J=8.6 Hz), 6.87 (s, 1H), 6.73 (s, 1H), 6.03 (s, 1H), 6.02 (s, 1H), 3.95 (m, 1H), 2.7 (obscured, m, 2H), 1.24 (d, 3H, J=6.1 Hz); mass spectrum, m/z (FD, $M^+$) 329; Anal. Calcd. for $C_{17}H_{15}NO_6$: C, 62.01; H, 4.59; N, 4.25. found C, 62.22, H, 4.79; N, 4.29.

EXAMPLE 6

Synthesis of (5RS, 7S)-7,8-dihydro-7-methyl-5-(4-nitrophenyl)-5H-1,3-dioxolo[4,5-G][2]benzopyran-5-ol 15 grams of the Example 4 intermediate (derived from the *Z. rouxii*-mediated ketone reduction) was dissolved in a solution of 75 mL of dimethylsulfoxide and 75 mL of dimethylformamide. The solution was cooled to 7°–9° C. and then aereated with 40% oxygen in nitrogen. 7.62 grams of 50% sodium hydroxide in water was added and the resulting mixture was stirred for 3–4 h. The reaction was terminated and while maintaining the temperature <120 C, 120 mL of toluene was added followed by a mixture of 45 mL of water and 10 mL hydrochloric acid. The phases were separated and the organic layer was washed with 75 mL of a 10% aqueous sodium thiosulfate solution. The organic layer containing the subtitled intermediate was carried into the next step.

EXAMPLES 7–9

0.5 ml of frozen yeast suspension containing the microorganism of Table 1 was added to 50 ml of a yeast-malt medium in a 250 ml flask. After 48 hours of shaking, 1.0 ml of culture is added to an additional 50 ml of medium and shaken for 48 more hours. 3,4-methylenedioxyphenyl acetone is added until the final concentration is 10 grams/liter along with 1 ml of 10% glucose. The cultures are incubated and shaken for 24 hours, then analyzed by HPLC for presence of the chiral alcohol intermediate of Example 1.

TABLE 1

| Ex. # | Micro organism | | Source | % Conversion | % EE |
|---|---|---|---|---|---|
| 7 | Candida famata | (C.f.) | A.T.C.C. 26418 | 0.0 | — |
| 8 | Zygosaccharomyces rouxii | (Z.r.) | A.T.C.C. 14462 | 77.8 | 99.5 |
| 9 | Mortierrela isobellina | (M.i.) | N.R.R.L. 1557 | 1.7 | 94.3 |

EXAMPLE 10

Synthesis of (S)-1-[(4-nitrophenyl)-|5-|4-(2-hydroxypropyl)-1,2-methylenedioxvphenyl]]|-2-phenyldiazane To a solution of the product of Example 5 (1.30 g) in 20 mL ethanol was added phenylhydrazine (0.45 g). The resulting solution was heated to reflux for 12 h. The mixture was cooled to room temperature and diluted with dichloromethane and washed with water and brine. The organic solution was dried over magnesium sulfate, filtered and concentrated by rotary evaporation. The residue was purified by silica gel chromatography (50% EtOAc in hexanes) to give 1.52 g of a 1:1 isomeric mixture of the title compound (91%).

TLC $R_f$ 0.43 (50% EtOAc/Hex); $^1$H NMR (CDCl$_3$, 300 MHz) δ 8.17 (d, 2H, J=9 Hz), 7.70 (m, 3H), 7.31 (m, 2H), 7.14 (m, 2H), 6.94 (m, 1H), 6.59 (d, 1H, J=9 Hz), 6.08 (m, 2H), 3.93 (m, 1H), 2.41 (m, 2H), 1.10 (2d, 3H, J=6.3 Hz)

EXAMPLE 11

Synthesis of (S)-1-[(4-nitrophenyl)-|5-|4-(2-hydroxypropyl)-1,2-methylenedioxyohenyl]]]-2-(2-pyridyl)diazane To a solution of the product of Example 5 (1.68 g) in 25 mL ethanol was added 2-hydrazinopyridine (0.70 g). The resulting mixture was heated to reflux for 24 h. The solution was cooled to room temperature and concentrated by rotary evaporation. The residue was dissolved in ethyl acetate and washed with water and brine. The organic solution was dried over magnesium sulfate, filtered and concentrated by rotary evaporation. The residue was purified by silica gel chromatography (50% EtOAc in hexanes) to give 1.30 g of the title compound (61%).

$^1$H NMR (CDCl$_3$, 300 MHz) δ 8.17 (dd, 2H, J=1.8, 7 Hz), 8.07 (m, 1H), 7.74 (m, 3H), 7.51 (m, 1H), 6.98 (d, 1H, J=7), 6.83 (m, 1H), 6.59 (d, 1H, J=4 Hz), 6.05 (dd, 2H, J=1.3, 8 Hz), 3.84 (m, 1H), 2.40 (m, 2H), 1.06 (d, 3H, J=6.1 Hz).

EXAMPLE 12

Synthesis of (S)-1-[4-nitrophenyl)-[5-[4-(2-hydroxypropyl)-1,2-methylenedioxyphenyl]]]-2-(1-phthalazinyl)diazane To a solution of the Example 5 intermediate (3.78 g) in 50 mL ethanol was added sodium bicarbonate (0.8 g) and hydralazine hydrochloride (2.2 g). The resulting heterogeneous mixture was heated to reflux for 12 h. The mixture was cooled to room temperature and the mixture was poured into rapidly stirred ice water (50–100 mL). The mixture was stirred for 30 min and the resulting precipitate was isolated by filtration. The orange solid was washed with water and a small portion of ether. The solid was dried in a vaccuum oven at 60° C. for 72 h to give 4.3 g of the desired product (80%) as a mixture of isomers (ca 9:1).

$^1$H NMR (CDCl$_3$, 300 MHz, major isomer) δ 10.7 (br s, 1H), 8.20 (d, 2H, J=9 Hz), 7.98 (m, 2H), 7.84 (d, 2H, J=9 Hz), 7.65 (m, 3H), 6.91 (s, 1H), 6.49 (s, 1H), 6.05 (s, 2H), 3.99 (m, 1H), 3.92 (br s, 1H), 2.60 (dd, 1H, J=2, 14 Hz), 2.17 (dd, 1H, J=10, 14 Hz), 1.11 (d, 3H, J=6 Hz).

EXAMPLE 13

Synthesis of (R)-7-phenyl-8,9-dihydro-8-methyl-5-(4-nitrophenyl)-7H-1,3-dioxolo[4,5-h||2,3] benzodiazepine To a solution of the product of Example 10 (0.64 g) in 6 mL dichloromethane cooled to 0° C. was added triethylamine (0.24 g) followed by methanesulfonyl chloride (0.2 g). After 0.5 h, the mixture was warmed to room temperature and diluted with dichloromethane. The solution was washed sequentially with 1N HCl, water and saturated sodium bicarbonate. The organic solution was dried over magnesium sulfate, filtered and concentrated to give an orange solid (0.81 g). A portion of the solid (0.66 g) was dissolved in 6 mL tetrahydrofuran and cooled to 0° C. Lithium t-butoxide (0.2 g) was added in one portion. After 0.5 h, the solution was diluted with ethyl acetate and then washed sequentially with saturated ammonium chloride, water and brine. The organic solution was dried over magnesium sulfate, filtered and concentrated. The residue was purified by silica gel chromatography (60% EtOAc in hexanes) to give 0.28 g of the title compound (51%).

TLC Rf=0.81 (60% EtOAc in hexanes); $^1$H NMR (CDCl$_3$, 300 MHz) δ 8.20 (dd, 2H, J=2.3, J=9.4 Hz), 7.78 (dd, 2H, J=2.3, J=9.3 Hz), 7.3 (m, 4H), 6.95 (m, 1H), 6.74 (s, 1H), 6.58 (s, 1H), 5.97 (s, 2H), 4.93 (m, 1H), 3.13 (dd, 1H, J=2.6, J=14.4 Hz), 2.83 (dd, 1H, J=7.0, 14.4 Hz), 1.10 (d, 3H, J=6.5 Hz); $^{13}$C NMR (CDCl$_3$, 75 MHz) δ 148.5, 148.4, 148.0, 147.1, 146.2, 144.1, 134.8, 129.8, 129.1, 126.8, 123.5, 121.2, 116.3, 109.6, 109.3, 101.6, 61.9, 39.5, 18.9.

EXAMPLE 14

Synthesis of (R)-7-(2-pyridyl)-8,9-dihydro-8-methyl-5-(4-nitrophenyl)-7H-1,3-dioxolo[4,5-h][2,3] benzodiazepine To a solution of the product of Example 11 (0.452 g) in 5 mL dichloromethane, cooled to 0° C., was added triethylamine (0.17 g) followed by methanesulfonyl chloride (0.15 g). After 0.5 h, the mixture was warmed to room temperature and diluted with dichloromethane. The solution was washed with 15 mL portions of brine (2×) and water (2×). The organic solution was dried over magnesium sulfate, filtered and concentrated by rotary evaporation to give a yellow solid (0.594 g). A portion of the ye llow solid (0.45 g) was dissolved in 6 mL tetrahydrofuran and cooled to 0° C. Lithium t-butoxide (0.13 g) was added in one portion. The mixture was warmed to room temperature after 0.75 h and stirring was continued for 3 h. The mixture was diluted with ethyl acetate. The resulting solution was washed with a saturated ammonium chloride solution, water and brine. The solution was dried over magnesium sulfate filtered and concentrated. The residue was purified by silica gel chromatography (60% EtOAc in hexanes) to give 0.25 g of the title compound (68%).

TLC Rf=0.81 (60% EtOAc in hexanes); $^1$H NMR (CDCl$_3$, 300 MHz) δ 8.23 (m, 3H), 7.76 (d, 2H, J=8.7 Hz), 7.58

(m, 1H), 7.50 (m, 1H), 6.80 (m, 1H), 6.75 (s, 1H), 6.54 (s, 1H), 5.97 (m, 2H), 5.82 (m, 1H), 3.19 (d, 1H, J=14.4 Hz), 2.88 (dd, 1H, J=6.9, 14.5 Hz), 1.05 (d, 3H, J=6.3 Hz); $^{13}$C NMR (CDCl$_3$, 75 MHz) δ 158.1, 148.5, 148.4, 147.2, 147.1, 146.0, 143.5, 137.6, 135.5, 129.9, 126.6, 123.5, 116.0, 111.0, 109.8, 109.7, 101.6, 57.7, 39.2, 18.8.

EXAMPLE 15

Synthesis of (R)-7-(1-phthalazinyl)-8,9-dihydro-8-methyl-5-(4-nitrophenyl)-7H-1,3-dioxolo|4,5-h||2,3| benzodiazepine To a solution of the title compound of Example 12 (0.26 g) and triethylamine (0.083 g) in 15 mL dichloromethane was added a solution of methanesulfonyl chloride (0.07 g) in 2 mL dichloromethane. Additional methanesulfonyl chloride (0.07 g) and triethylamine (0.08 g) were added to complete the reaction. The organic solution was washed with brine and then dried over sodium sulfate, filtered and concentrated.

The residual oil was dissolved in ethyl acetate and washed with 1N NaOH (3×). The organic solution was dried over sodium sulfate, filtered and concentrated to give 0.33 g of an orange liquid. The residue was dissolved in 10 mL tetrahydrofuran and lithium t-butoxide (0.087 g) was added. The resulting solution was stirred overnight. The mixture was diluted with ethyl acetate and washed with water and brine. The organic solution was dried over sodium sulfate, filtered and concentrated. The residue was purified by silica gel chromatography (4:1:1 hexanes, acetone,chloroform) to give 0.11 g of the title compound (45%) as a yellow solid and 0.05 g of the corresponding elimation product (21%).

TLC R$_f$=0.22 (50% EtOAc in hexanes); $^1$H NMR (CDCl$_3$, 500 MHz): δ δ 9.25 (s, 1H), 8.19–8.16 (m, 3H), 7.90 (d, 1H, J=7.9 Hz), 7.82 (t, 1H, J=7.3 Hz), 7.76–7.73 (m, 3H), 6.89 (s, 1H), 6.69 (s, 1H), 6.05 (d, 2H, J=3.8 Hz), 5.97–5.94 (m, 1H), 3.32 (dd, 1H, J=3.8, 14.4 Hz), 2.88 (dd, 1H, J=5.2, 14.4 Hz), 1.31 (d, 3H, J=6.3 Hz); $^{13}$C NMR (CDCl$_3$, 125 MHz): δ 157.73, 153.32, 149.39, 148.94, 148.22, 146.68, 145.98, 136.04, 131.93, 131.66, 130.06, 129.66, 126.93, 126.79, 126.73, 123.88, 123.55, 110.28, 109.16, 102.09, 63.20, 39.33, 19.35.

EXAMPLE 16

Synthesis of (R)-7-phenyl-8,9-dihydro-8-methyl-5-(4-aminophenyl)-7H-1,3-dioxolo[4,5-h][2,3] benzodiazepine To a solution of the product of Example 13 (0.24 g) in 15 mL iso-propanol was added 10% Pd/C (100 mg) followed by a solution of potassium formate (0.13 g) in 0.5 mL water. Additional potassium formate (0.80 g) was added after 1.5 h. After 4 h, the reaction mixture was filtered through diatomaceous earth and concentrated. The residue was dissolved in ethyl acetate which was then washed with water and brine. The organic solution was dried over magnesium sulfate, filtered and concentrated by rotary evaporation. The residue was purified by silica gel chromatography (33% EtOAc in hexanes). The yellow solid was dissolved in ethanol and concentrated (2×) then dried in a vacuum oven at 50° C. for 12 h to give 0.135 g of the title compound (61%).

TLC R$_f$=0.33 (33% EtOAc in hexanes); mp 118°–119° C.; MS (FD+), m/z 371; $^1$H NMR (CDCl$_3$, 300 MHz) δ 7.6 (dd, 2H, J=1.8, J=6.7 Hz), 7.24 (m, 2H), 7.02 (d, 2H, J=7.8 Hz), 6.77 (m, 2H), 6.70 (m, 2H), 6.61 (s, 1H), 5.98 (d, 1H, J=1.3 Hz), 5.91 (d, J=1.3 Hz), 4.8 (m, 1H), 3.89 (br s, 2H), 2.74 (m, 2H), 1.24 (d, 3H, J=6.2 Hz); $^{13}$C NMR (CDCl$_3$, 75 MHz) δ 166.8, 149.2, 148.4, 148.3, 145.9, 135.4, 130.8, 128.8, 128.7, 127.9, 118.6, 115.3, 114.5, 109.3, 108.2, 101.3, 64.5, 40.1, 16.16.

EXAMPLE 17

Synthesis of (R)-7-(2-pyridyl)-8,9-dihydro-8-methyl-5-(4-aminophenyl)-7H-1,3-dioxolo|4,5-h||2, 3|benzodiazepine To a solution of the product of Example 14 (0.17 g) in 10 mL iso-propanol was added 10% Pd/C (0.9 g) followed by a solution of potassium formate (0.09 g) in 0.5 mL water. Additional potassium formate (0.05 g) was added after 1 h. After 2 h, the reaction mixture was filtered through diatomaceous earth and concentrated. The residue was dissolved in ethyl acetate which was then washed with water and brine. The organic solution was dried over magnesium sulfate, filtered and concentrated by rotary evaporation. The residue was purified by silica gel chromatography (50% EtOAc in hexanes). The yellow solid was dissolved in ethanol and concentrated (2×) then dried in a vacuum oven at 50° C. for 12 h to give 0.12 g of the title compound (75%).

TLC R$_f$=0.6 (50% EtOAc in hexanes); mp 128°–130° C; MS (FD+), m/z 372; $^1$H NMR (CDCl$_3$, 300 Mz) δ 8.17 (m, 1H), 7.61 (d, 2H, J=6.8 Hz), 7.46 (m, 1H), 6.97 (d, 1H, J=8.5 Hz), 6.80 (s, 1H), 6.75 (d, 2H, J=9.0 Hz), 6.68 (m, 2H), 5.98 (d, 1H, J=1.3 Hz), 5.92 (d, 1H, 1.3 Hz), 5.50 (m, 1H), 3.92 (br s, 2H), 2.78 (m, 2H), 1.26 (d, 3H, J=6.4 Hz); $^{13}$C NMR (CDCl$_3$, 75 Mz) δ 167.1, 159.4, 148.6, 148.4, 147.2, 145.8, 137.0, 136.0, 130.9, 128.2, 127.8, 114.4, 113.7, 110.5, 109.4, 108.5, 101.3, 63.0, 39.6, 17.3.

Anal Calcd. for C$_{22}$H$_{20}$N$_4$O$_2$: C,70.95;H,5.41;N,15.04. Found: C,70.76; H 5.71; N 14.93

EXAMPLE 18

Synthesis of (R)-7-(1-phthalazinyl)-8,9-dihydro-8-methyl-5-(4-aminophenyl)-7H-1,3-dioxolo[4,5-h][2, 3]benzodiazepine To a solution of the product of Example 15 (0.11 g) in 20 mL iso-propanol was added 10% Pd/C (0.053 g) followed by a solution of potassium formate (0.073 g) in <0.5 mL water. Additional potassium formate was added in three portions over 6 h. The mixture was stirred overnight, filtered through diatomaceous earth and concentrated by rotary evaporation. The residue was dissolved in ethyl acetate and washed with water and brine. The organic solution was dried over sodium sulfate, filtered and concentrated. The residue was purified by silica gel chromatography (gradient: 1:1 chloroform: ethyl acetate then 1:4 chloroform: ethyl acetate). The isolated material was dissolved in ethanol and concentrated then dissolved in chloroform/hexane and concentrated. The yellow solid was dried in a vacuum oven at 55° C. for 18 h to give 75.3 mg of the title compound (73%).

yellow solid, mp 230 (dec); TLC Rf=0.2 (50% chloroform in ethyl acetate); $^1$H NMR (CDCl$_3$, 500 MHz): δ 9.05 (s, 1H), 8.00 (d, 1H, J=8.4 Hz), 7.76 (d, 1H, J=7.8 Hz), 7.71–7.68 (m, 1H), 7.65–7.62 (m, 1H), 7.53 (d, 2H, J=8.6 Hz), 6.87 (s, 1H), 6.80 (s, 1H), 6.65 (d, 2H, J=8.5 Hz), 6.00–5.95 (m, 2H), 5.70–5.66 (m, 1H), 4.35–3.80 (br s, 2H), 3.00 (dd, 1H, J=6.1, 13.8 Hz), 2.72 (dd, 1H, J=7.9, 13.8 Hz), 1.47 (d, 3H, J=5.9 Hz); $^{13}$C NMR (CDCl$_3$): δ 170.32, 157.34, 149.64, 149.07, 147.15, 146.39, 136.16, 131.28, 130.85, 129.49, 128.71, 126.86, 126.67, 126.37, 123.26, 114.84, 109.33, 108.84, 101.80, 64.88, 39.54, 17.82.

EXAMPLE 19

Alternative synthesis of (S)-α-methyl-1, 3-benzodioxole-5-ethanol

To a suspension of magnesium turnings (17 g) in 50 mL tetrahydrofuran was added dropwise a solution of 5-bromo-1,3-benzodioxole (93.6 g). After complete addition, the mixture was diluted with 250 mL tetrahydrofuran and the resulting mixture was stirred overnight. 13 mL of the solution (0.78M) was transferred to a round bottom flask containing copper (I) iodide (0.12 g). The resulting mixture was cooled to −50 ° C. and a solution of (S)-(-)-propylene oxide in 3 mL tetrahydrofuran was slowly added then stirred 10 min. The mixture was diluted with ether. The isolated organic phase was washed with water and brine. The aqueous wash was extracted with ether (2×) and the combined organic solutions were dried over magnesium sulfate, filtered and concentrated. The residue was purified by silica gel chromatography (50% ether in pentane) to give 1.66 g of the desired product (91%). Chiral HPLC analysis indicated that the optical purity of the material was 98.3%.

EXAMPLE 20

Synthesis of (R)-7-(2-benzothiazolyl)-8,9-dihydro-8-methyl-5-(4-nitrophenyl)-7H-1,3-dioxolo[4,5-h][2,3]benzodiazepine To a solution of the product of Example 5 (1.00 g) in 25 mL ethanol with several drops of concentrated HCl was added 2-hydrazinobenzothiazole (0.63 g). The resulting solution was heated to reflux for 12 h. The mixture was cooled to room temperature and the solvent was evaporated. The residue was extracted with ethyl acetate and washed with brine. The organic solution was dried over sodium sulfate, filtered and concentrated by rotary evaporation. A portion of the residue (1.0 g) was dissolved in 25 mL dichloromethane and cooled to 0° C. Triethylamine (1.0 ml) and methanesulfonyl chloride (0.58 ml) were then added portion wise over several hours. After stirring overnight at room temperature, the mixture was washed sequentially with 1N HCl, brine, 1N NaOH and brine. The organic solution was dried over sodium sulfate, filtered and concentrated to give an brown oil (1.15 g). A portion of the oil (0.95 g) was dissolved in 350 mL ethanol and cooled to 0° C. Sodium hydroxide solution (0.09 ml, 19M) was added in one portion. After 0.75 h, the solution was evaporated. The residue was extracted with ethyl acetate and then washed sequentially with water, brine, saturated sodium bicarbonate and brine. The organic solution was dried over sodium sulfate, filtered and concentrated. The residue was purified by silica gel chromatography (25% hexanes in chloroform) to give 0.69 g of the title compound.

TLC $R_f$=0.37 (25% $CHCl_3$ in hexanes); yellow solid, mp 259.4–260.6; $^1$H NMR ($CDCl_3$, 500 MHz): δ 8.30 (d, 2H, J=8.7 Hz), 7.83 (d, 2H, J=8.7 Hz), 7.71 (d, 2H, J=8.3 Hz), 7.37 (t, 1H, J=7.9 Hz), 7.20 (t, 1H, J=7.4 Hz), 6.82 (s, 1H), 6.61 (s, 1H), 6.06–6.04 (m, 2H), 5.69–5.66 (m, 1H), 3.37 (d, 1H, J=14.8 Hz), 2.97 (dd, 1H, J=6.1, 14.8 Hz), 1.25 (d, 3H, J=6.6 Hz); $^{13}$C NMR ($CDCl_3$, 125 MHz): δ 170.15, 152.88, 149.66, 148.12, 147.19, 146.76, 146.14, 135.63, 133.25, 130.52, 126.17, 125.83, 123.91, 122.92, 121.29, 120.94, 110.58, 110.52, 102.21, 62.36, 39.02, 19.28; IR (KBr, $cm^{-1}$): 1506.6 (s), 1483.2 (s), 1441.0 (m), 1389.9 (m), 1335.9 (s), 1270.3 (m), 1233.6 (m), 1189.3 (m), 1110.2 (m), 1034.0 (m), 1012.8 (m), 910.5 (m), 866.2 (m), 851.9 (s), 754.3 (s), 692.5 (m); mass spectrum (FD), m/z 458.0.

EXAMPLE 21

Synthesis of (R)-7-(2-benzothiazolyl)-8,9-dihydro-8-methyl-5-(4-aminophenyl)-7H-1,3-dioxolo[4,5-h][2,3]benzodiazepine To a solution of the product of Example 20 (0.55 g) in 300 mL iso-propanol and 25 ml dimethylformamide was added 10% Pd/C (250 mg) followed by a solution of potassium formate (0.30 g) in 1.0 mL water. Additional potassium formate (1.50 g) was added in five portions over the course of 5 h. After stirring overnight, the reaction mixture was filtered through diatomaceous earth and concentrated. The residue was dissolved in ethyl acetate which was then washed with water and saturated sodium bicarbonate. The organic solution was dried over sodium sulfate, filtered and concentrated by rotary evaporation. The residue was purified by silica gel chromatography (4/2/1 chloroform/hexanes/EtOAc) to give 0.31 g of the desired product (62%).

TLC $R_f$=0.35 (4/2/1 chloroform/hexanes/EtOAc); yellow solid, mp gel at 145; $^1$H NMR ($CDCl_3$, 500 MHz): δ 7.68–7.59 (m, 4H), 7.32–7.29 (m, 1H), 7.12–7.09 (m, 1H), 6.83 (s, 1H), 6.75–6.72 (m, 2H), 6.69 (s, 1H), 6.01 (m, 2H), 5.46–5.42 (m, 1H), 3.97 (s, 2H), 3.02 (dd, 1H, J=4.6, 14.1 Hz), 2.86 (dd, 1H, J=9.9, 14.1 Hz), 1.40 (d, 3H, J=6.3 Hz); $^{13}$C NMR ($CDCl_3$, 125 MHz): δ 170.42, 165.62, 153.45, 149.57, 149.43, 146.50, 135.97, 132.97, 131.68, 127.57, 127.54, 126.07, 121.86, 121.25, 120.13, 114.75, 110.58, 109.43, 101.98, 66.86, 39.31, 18.43; IR (KBr, $cm^{-1}$): 1619.5 (m), 1605.4 (m), 1510.5 (s), 1484.4 (s), 1442.9 (s), 1379.3 (m), 1273.2 (m), 1235.6 (m), 1172.9 (m), 1036.9 (m), 752.3 (m), 726.3 (m); mass spectrum (FD), m/z 428.0.

EXAMPLE 22

Synthesis of (R)-7-(2-benzimidazolyl)-8,9-dihydro-8-methyl-5-(4-nitrophenyl)-7H-1,3-dioxolo[4,5-h][2,3]benzodiazepine To a solution of the product of Example 5 (1.79 g, 5.43 mmol) in 20 mL of ethanol was added 2-hydrazinobenzimidazole (0.96 g, 6.51 mmol). The resulting brown slurry was heated to reflux and after 30 min, 3 drops of conc. HCl were added. After 3 h, another 3 drops conc. HCl were added to the dark, red reaction mixture. The mixture was heated at reflux for 2 days then cooled to room temperature and partitioned between ethyl acetate and saturated aqueous $NaHCO_3$. The organic layer was washed with brine and dried ($Na2SO_4$) before being concentrated by rotary evaporation. The residue was crystallized out of ethyl acetate then dissolved in ethyl acetate and ethanol and washed with 0.5M HCl, saturated aqueous $NaHCO_3$, then brine. The organic solution was dried over $Na_2SO_4$, filtered, evaporated to near dryness, then crystallized out of 50 mL of ethyl acetate to afford 876 mg of (S)-1-[(4-nitrophenyl)-[5-[4-(2-hydroxypropyl)-1,2-methylenedioxyphenyl]]]-2-(2-benzimidazolyl)diazane. A portion of the resulting dried solids (800 mg, 1.75 mmol) was dissolved in 40 mL of tetrahydrofuran. Triphenyl phosphine (551 mg, 2.10 mmol) was added and the resulting solution was cooled in an ice water/NaCl bath. A solution of diisopropyl azodicarboxylate (430 mL, 2.18 mmol) in 5 mL of tetrahydrofuran was added dropwise over 8 minutes and the resulting dark solution was stirred for 30 min then partitioned between ethyl acetate and brine. The organic layer was dried over $Na_2SO_4$, filtered, and evaporated to an orange oil which was purified by silica gel chromatography (40% ethyl acetate in hexanes) to afford 688 mg of the title compound.

¹H NMR (CDCl₃, 300 MHz) δ 1.20 (d, 3, J=8); 3.00 (dd, 1, J=6, 15); 3.34 (d, 1, J=15); 5.72 (m, 1); 6.02 (d, 2, J=3); 6.50 (s, 1), 6.79 (s, 1); 7.18 (m, 2); 7.32 (d, 1, J=8); 7.60 (d, 1, J=8); 7.72 (d, 2, J=9); 8.30 (d, 2, J=9); 9.18 (s, 1).

EXAMPLE 23

Synthesis of (R)-7-(2-benzimidazolyl)-8,9-dihydro-8-methyl-5-(4-aminophenyl)-7H-1,3-dioxolo[4,5-h][2,3]benzodiazepine To a solution of the product of Example 22 (669 mg, 1.52 mmol) in 20 mL of absolute ethanol under a N2 blanket was added 10% Pd/C (335 mg) followed by a solution of potassium formate (461 mg, 5.48 mmol) in 0.5 mL of water. After 1 h, the reaction mixture was filtered through a pad of celite and concentrated by rotary evaporation. The solid residue was partioned between ethyl acetate and water and the organic layer was washed with brine and dried over Na₂SO₄. Solvent was removed by rotary evaporation and the residue was purified by silica gel chromatography (40% hexanes in ethyl acetate) to afford 478 mg (76.5%) of the title compound. MS (FD+)=411. IR: 1623, 1543, 1486 cm⁻¹.
¹H NMR (CDCl₃, 300 MHz) δ 1.29 (d, 3, J=7); 2.82 (dd, 1, J=10, 14); 3.02 (dd, 1, J=4, 14); 3.96 (s, 2); 5.46 (m, 1); 6.00 (d, 2, J=8); 6.71 (m, 4); 7.08 (m, 2); 7.30 (s, 1); 7.52 (m, 3); 9.00 (s, 1).

EXAMPLE 24

Synthesis of (R)-7-(2-methoxycarbonylthien-3-yl)-8,9-dihydro-8-methyl-5-(4-nitrophenyl)-7H-1,3-dioxolo[4,5h][2,3]benzodiazepine To a solution of the product of Example 5 (3.52 g, 10.70 mmol) in 28 mL of ethanol was added methyl 3-hydrazinothiophene-2-carboxylate (2.01 g, 11.67 mmol) and the resulting solution was heated to reflux. After 1 h, 3 drops of conc. HCl was added and after another 1 h, the reaction mixture was allowed to cool to near room temperature and partitioned between ethyl acetate and 0.2M HCl. The organic layer was washed with 0.1M HCl, saturated aqueous NaHCO₃, then brine and dried over Na₂SO₄. The solvent was removed by rotary evaporation to afford 4.67 g of an orange solid. A portion of the solid material (2.086 g, 4.33 mmol) was dissolved under N₂ in 60 mL of tetrahydrofuran and the clear, orange solution was cooled in an ice water/NaCl bath. To the solution was added triethylamine (845 mL, 6.06 mmol) followed by methane sulfonyl chloride (445 mL, 5.64 mmol). After 90 min the reaction was quenched with 25 mL of water and partitioned with ethyl acetate. The organic layer was washed with 1M HCl then brine and dried over Na₂SO₄. The solvent was removed by rotary evaporation to afford 2.464 g of solid. A portion of the solid (2.088 g, 3.73 mmol) was dissolved under N₂ in 40 mL of tetrahydrofuran and the solution was cooled in an ice water bath. Lithium t-butoxide (328 mg, 4.10 mmol) was added and the reaction was stirred for 21 h. Another portion of lithium t-butoxide (33 mg, 0.41 mmol) was added and after 2 h, the reaction was quenched with 20 mL of saturated aqueous NH₄Cl. The mixture was extracted with ethyl acetate and the organic layer was washed with 1M HCl, 1:1 saturated aqueous NaHCO₃:brine, and brine, then dried over Na₂SO₄. Solvent was removed by rotary evaporation and the residue was purified by silica gel chromatography to afford 1.043 g of the title compound.

¹H NMR (CDCl₃, 300 MHz): δ 1.10 (d, 3, J=7); 2.72 (dd, 1, J=9, 14); 3.06 (dd, 1, J=5, 14); 3.76 (s, 3); 5.12 (m, 1); 6.00 (d, 2, J=6); 6.55 (s, 1); 6.87 (s, 1); 7.40 (m, 2); 7.79 (d, 2, J=9); 8.21 (d, 2, J =9).

EXAMPLE 25

Synthesis of (R)-7-(2-methoxycarbonylthien-3-yl)-8,9-dihydro-8-methyl-5-(4-aminophenyl)-7H-1,3-dioxolo[4,5-h][2,3]benzodiazepine To a solution of the product of Example 24 (794 mg, 1.71 mmol) in 16 mL of absolute ethanol and 3 mL of acetone under N₂ was added 10% Pd/C (400 mg) followed by a solution of potassium formate (513 mg, 6.10 mmol) in 1 mL of H₂O. After 50 min, the mixture was filtered through a pad of celite and concentrated by rotary evaporation. The residue was partitioned between ethyl acetate and water and the organic layer was washed with brine and dried over Na₂SO₄. The solvent was removed by rotary evaporation and the residue was purified by silica gel chromatography (1:1 ethyl acetate hexanes) to afford 682 mg of the desired final product.

¹H NMR (CDCl₃, 300 MHz): δ 1.13 (d, 3, J=6); 2.62 (dd, 1, J=11, 15); 2.78 (dd, 1, J=6, 13); 3.70 (s, 3); 3.88 (s, 2); 5.15 (m, 1); 5.95 (d, 2, J=15); 6.65 (m, 3); 6.88 (s, 1); 7.35 (d, 1, J=6); 7.48 (m, 3).

We claim:

1. A compound having the general formula:

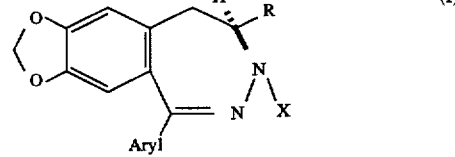

wherein R is hydrogen or $C_1$–$C_{10}$ alkyl;

X is an aromatic moiety selected from phenyl, thienyl, furyl, pyridyl, imidazolyl, benzimidazolyl, benzothiazolyl and phthalazinyl which is unsubstituted or substituted with one or more moieties chosen from the group consisting of halogen, hydroxy, cyano, nitro, $C_1$–$C_6$ alkyl, $C_3$–$C_6$ cycloalkyl, $C_1$–$C_4$ alkoxy, carboxy, $C_1$–$C_6$ alkoxycarbonyl, acetyl, formyl, carboxymethyl, hydroxymethyl, amino, aminomethyl, methylenedioxy and trifluoromethyl; and "Aryl" represents p-nitrophenyl, p-aminophenyl or p-(protected amino) phenyl;

or a pharmaceutically acceptable salt thereof.

2. A compound as claimed in claim 1, wherein Aryl represents p-aminophenyl or p-($C_1$–$C_6$) alkanoylaminophenyl.

3. A compound as claimed in claim 2, wherein Aryl represents p-aminophenyl.

4. A compound as claimed in claim 3, wherein R represents methyl.

5. A compound as claimed in claim 4, wherein X represents an aromatic moiety which is unsubstituted or substituted by one or more moieties chosen from the group consisting of halogen, hydroxy, cyano, nitro, $C_1$–$C_6$ alkyl, $C_1$–$C_4$ alkoxy, carboxy, acetyl, formyl, carboxymethyl, hydroxymethyl, amino, aminomethyl or trifluoromethyl.

6. A compound as claimed in claim 5, wherein the aromatic moiety is selected from phenyl, thienyl, furyl, pyridyl, imidazolyl and phthalazinyl.

7. A compound as claimed in claim 4, wherein X represents phenyl, 4-methylphenyl, 2-methylphenyl, 4-methoxyphenyl, 4-(i-propyl)phenyl, 4-cyclopentylphenyl, 4-(t-butyl)phenyl, 4-acetylphenyl, 4-trifluoromethylphenyl, 4-chlorophenyl, 2-bromophenyl, 3-iodophenyl or 3,4-(methylenedioxy)phenyl.

8. A compound as claimed in claim 4, wherein X is phenyl, 2-pyridyl, 2-methoxycarbonylthien-3-yl, 2-benzimidazolyl, 2-benzothiazolyl or 1-phthalazinyl.

9. A compound as claimed in claim 8, wherein X is phenyl, 2-pyridyl or 1-phthalazinyl.

10. (R)-7-(2-pyridyl)-8,9-dihydro-8-methyl-5-(4-aminophenyl)-7H-1,3-dioxolo[4,5-h][2,3]benzodiazepine, or a pharmaceutically salt thereof.

11. A pharmaceutical composition which comprises a compound as claimed in claim 1 together with a pharmaceutically acceptable diluent or carrier.

12. A method of treating convulsions in a mammal requiring such treatment, which comprises administering an effective amount of a compound of claim 1.

13. A method of blocking AMPA receptors in a mammal requiring such treatment, which comprises administering an effective amount of a compound of claim 1.

* * * * *